(12) United States Patent
Ko et al.

(10) Patent No.: US 7,803,424 B2
(45) Date of Patent: Sep. 28, 2010

(54) METHOD FOR MANUFACTURING METAL-CARRYING CARBONACEOUS MATERIAL

(75) Inventors: Tse-Hao Ko, Taichung (TW); Ming-Chain Hung, Taichung (TW)

(73) Assignee: Feng Chia University, Taichung (TW)

( * ) Notice: Subject to any disclaimer, the term of this patent is extended or adjusted under 35 U.S.C. 154(b) by 332 days.

(21) Appl. No.: 11/878,571

(22) Filed: Jul. 25, 2007

(65) Prior Publication Data

US 2008/0220162 A1    Sep. 11, 2008

(30) Foreign Application Priority Data

Mar. 9, 2007    (TW) .............................. 96108225 A

(51) Int. Cl.
 *B05D 7/00* (2006.01)
(52) U.S. Cl. .................. 427/217; 427/215; 427/227; 427/383.3; 205/180; 205/184; 205/185; 205/418
(58) Field of Classification Search ................. 427/215, 427/229; 502/418, 401
See application file for complete search history.

(56) References Cited

U.S. PATENT DOCUMENTS

| | | | | |
|---|---|---|---|---|
| 3,294,572 | A | * | 12/1966 | Salvatore et al. ............. 427/229 |
| 2004/0259728 | A1 | * | 12/2004 | Ko .............................. 502/417 |
| 2005/0279372 | A1 | | 12/2005 | Sundar et al. |
| 2006/0178262 | A1 | | 8/2006 | Rokicki et al. |
| 2006/0178263 | A1 | * | 8/2006 | Tatsuhara et al. ........... 502/417 |
| 2006/0205963 | A1 | | 9/2006 | Rubinstein et al. |
| 2007/0122461 | A1 | * | 5/2007 | Ko .............................. 424/445 |

FOREIGN PATENT DOCUMENTS

| | | | |
|---|---|---|---|
| CN | 1103054 | | 5/1995 |
| JP | 57019083 | | 2/1982 |
| JP | 10099678 | | 4/1998 |
| KR | 2005117961 | A * | 12/2005 |

OTHER PUBLICATIONS

Paul et al. Handbook of Industrial Mixing, John Wiley & Sons, Inc., Hoboken, New Jersey. 2004.*
Oya, A. et al., "Preparation of Pitch-Based Antibacterial Activated Carbon Fiber," *Carbon*, vol. 31, No. 8, pp. 1243-1247, 1993.
Li, Ch. Y., et al., "Antibacterial Pitch-Based Activated Carbon Fiber Supporting Silver," *Carbon*, vol. 36, Nos. 1-2, pp. 61-65, 1998.
Wang, Y. L. et al., "Preparation and Characterization of Antibacterial Viscose-Based Activated Carbon Fiber Supporting Silver," *Carbon*, vol. 36, No. 11, pp. 1567-1571, 1998.

* cited by examiner

*Primary Examiner*—Timothy H Meeks
*Assistant Examiner*—Collette Ripple
(74) *Attorney, Agent, or Firm*—Tim Tingkang Xia; Morris, Manning & Martin LLP

(57) ABSTRACT

A method for manufacturing a metal-carrying carbonaceous material is provided. The method comprises immersing a carbonaceous material in a metal-containing aqueous solution under vacuum, with stirring, and/or in the presence of a polar solvent, and then thermally treating the immersed carbonaceous material at a temperature ranging from 120° C. up to a temperature not higher than the melting point of the involved metal under vacuum or in the presence of a protective gas. According to the method, the metal can be effectively carried on a carbonaceous material so as to enhance the applicability of the metal-carrying carbonaceous material.

23 Claims, 4 Drawing Sheets

METHOD FOR MANUFACTURING METAL-CARRYING CARBONACEOUS MATERIAL

This application claims priorities to Taiwan Patent Application No. 096108225 filed on 9 Mar, 2007.

CROSS-REFERENCES TO RELATED APPLICATIONS

Not applicable.

FIELD OF THE INVENTION

The subject invention relates to a method for manufacturing a metal-carrying carbonaceous material, especially a carbonaceous material carrying nano-sized metal particles. In particular, the subject invention relates to a method for manufacturing a carbonaceous material carrying nano-sized silver particles.

BACKGROUND OF THE INVENTION

It is known that metals, such as silver, gold, palladium, platinum, copper, and zinc, effectively kill microbes. Therefore, many applications of using the antimicrobial effect of such metals have been proposed. An example of such application is a wound dressing. Moreover, it has been disclosed that a noble metal such as silver and an activated carbon are used together in the water treatment of wastewater and drinking water. For recycling use, silver is preferably carried on the activated carbon. The activated carbon can remove the impurities in water, while the silver can kill the microbes on the activated carbon. Contamination resulting from the growth of microbes due to the bioaffinity of the activated carbon is thereby, prevented.

The usage form of the activated carbon comprises activated carbon fiber, activated carbon granule, and activated carbon powder. Recently developed in the 70's, the activated carbon fiber is an adsorption material with superior performance. Compared to the conventional granulated or powdered activated carbon, the activated carbon fiber similarly has a large number of open pores, superior adsorption property, good antibiotic resistance, hydrophilic property, electron supply ability, and high specific surface area. However, the activated carbon fiber has a different molecular structure, appearance, and structures of pores on the surface. Specifically, the activated carbon fiber allows for more diffusion during adsorption and desorption and can be fabricated into various forms, such as felt or cloth, in a second process. Moreover, the activated carbon fiber has a greater specific surface area and adsorption efficiency and is readily utilized.

Ling Wang, Shurong Li and Fenggang An disclosed in CN1103054 (1995) that the market selling pure charcoal was washed with distilled water. After drying and cooling, it was co-impregnated with a prepared solution of $AgNO_3$ and $NH_3H_2O$ and vibrated. After removing the water phase, re-drying and cooling, it was co-impregnated with a prepared solution of KI and vibrated, and then a silver-containing activated carbon was obtained after drying, washing and re-drying. The silver-containing activated carbon could then be used as a filtering material in the mineral spring pot to inhibit the bacterial growth in the pot so as to increase the quality of drinking water.

Suzuki Mitsuo, Hirahara Satoshi, and Okurama Kohei disclosed in JP10099678 (1998) that a silver compound was added to a raw material of activated carbon, i.e., coal, before manufacturing the activated carbon. The mixture was then subjected to heat treatment and an activation process to obtain a silver-containing activated carbon.

Okura Yukio disclosed in JP57019083 (1982) that the activated carbon was first immersed in a silver compound, e.g., silver salt. Then, steam was injected into the immersed activated carbon for a heat treatment at a temperature slightly lower than the melting point of the silver salt to produce a silver-containing activated carbon.

To form silver on activated carbon fibers for the antibacterial effect, A. Oya, T. Wakahara, and S. Yoshida mentioned in *Carbon,* 31, 1243-1247, 1993 that a silver acetate solution was mixed with pitch, and then spun and stabilized. Afterwards, the activation process was conducted using steam at a temperature of 900° C. to manufacture activated carbon fiber containing up to 0.03 wt % of silver. Nonetheless, Oya et al. consider that this method still had problems which included improving the spinning process, controlling activation conditions and finding a way to produce silver-containing activated carbon fibers with a high specific surface area.

C. Y. Li, Y. Z. Wan, J. Wang, Y. L. Wang, X. Q. Jiang, and L. M. Han mentioned in *Carbon,* 36, 61-65, 1998 that pitch-based activated carbon fiber was impregnated in an unsaturated silver nitrate solution for 12 hours and then thermally cracked in nitrogen gas at a temperature of 420° C. for 30 minutes to obtain a silver-containing pitch-based activated carbon fiber. However, Li et al. considered that this method still was unable to evenly distribute the silver particles and prevent the precipitation of silver in water.

The inventors of the subject application repeated the method provided by Li et al. and also found the above drawbacks. The impregnation process used by Li et al. was the same as that disclosed in CN1103054 and JP5701908 and the results were identical. All of the problems, such as the size and distribution of silver particles and their precipitation in water, could not be resolved.

Furthermore, as known by persons skilled in the art, the noble metals often have a catalytic function, in addition to an antibacterial benefit. For example, it has been known that silver can be used in the following catalytic applications: the catalytic oxidation of olefins for preparing olefin oxides, the selective catalytic hydrogenation of acetylene in an ethylene stream for purifying the ethylene stream, and the catalytic oxidation of carbon monoxide in cigarette smoke for converting it to carbon dioxide. The aforementioned catalytic applications can be found in US2006/0178262A1, US2006/0205963A1, and US2005/0279372A1, which are incorporated hereinto for reference.

Given the above concerns, it is now important to find a proper process for effectively carrying a metal, such as silver, on a substrate much like a carbonaceous material with a high specific surface area to enhance its applicability.

The subject invention improves on the method for manufacturing a metal-carrying carbonaceous material. In particular, the method provides a carbonaceous material with a low metal leachability in water, especially a carbonaceous material which conforms to the drinking water standard of the United States, i.e., having a silver leachability of lower than 50 ppb.

SUMMARY OF THE INVENTION

Unless it is specially described, the carbonaceous material mentioned in the subject application is selected from a group consisting of: activated carbon, graphite, carbon, or a combination thereof. Moreover, unless it is specially described, all of the mentioned carbonaceous materials can be in the form of powder, granule, fiber, sheet, or a product of any combination of the foregoing forms. For example, the carbonaceous material can be an activated carbon fiber or fabric, granulated or powdered charcoal, and/or porous graphite such as flexible graphite or extended graphite. The carbonaceous material can also be a sheet laminated from powdered and/or granulated activated carbon, powdered and/or granulated porous graphite, or a combination thereof.

One objective of the subject invention is to provide a method for manufacturing a metal-carrying carbonaceous material comprising the following procedures:
(a) impregnating a carbonaceous material in a metal-containing aqueous solution;
(b) thermally treating the impregnated carbonaceous material at a temperature ranging from 120° C. to a temperature not higher than the melting point of the metal under vacuum or in the presence of a protective gas;
wherein step (a) is conducted under one or more of the following conditions:
(a1) under vacuum;
(a2) with stirring; and
(a3) with the presence of a polar solvent in the aqueous solution, and
wherein the metal is selected from a group consisting of: silver, cobalt, nickel, zinc, gold, copper, platinum, palladium, iron, and a combination thereof, with a proviso that if the metal is silver and step (a) is conducted under condition (a1) only, step (b) is operated at a temperature of above 450° C.

Another objective of the subject invention is to provide a method for manufacturing a nano-sized metal-carrying carbonaceous material comprising the following steps:
(a) impregnating a carbonaceous material in a metal-containing aqueous solution;
(b) thermally treating the impregnated carbonaceous material at a temperature higher than 500° C. but not higher than the melting point of the metal under vacuum or in the presence of a protective gas;
wherein step (a) is conducted under one or more of the following conditions:
(a1) under vacuum;
(a2) with stirring; and
(a3) with the presence of a polar solvent in the aqueous solution, and
wherein the metal is selected from a group consisting of: silver, cobalt, nickel, zinc, gold, copper, platinum, palladium, iron, and a combination thereof.

In the subject invention, if one objective of the subject invention is to kill microbes, it is preferred for the activated carbon or porous graphite to be the carbonaceous material. It is believed that the activated carbon/porous graphite can aggregate and absorb microbes on its surface due to the electrostatic interactions or van der Waal forces between the microbes and the surface of the activated carbon/porous graphite, as well as the bioaffinity of the activated carbon/ porous graphite. Consequently, the subject invention adopts an active manner in aggregating and destroying the microbes around the metal to provide a superior antimicrobial effect The detailed technology and preferred embodiments of the subject invention are described in the below so that persons having ordinary skill in the art can understand the features of the subject invention.

DESCRIPTION OF THE INVENTION

Figure 1:
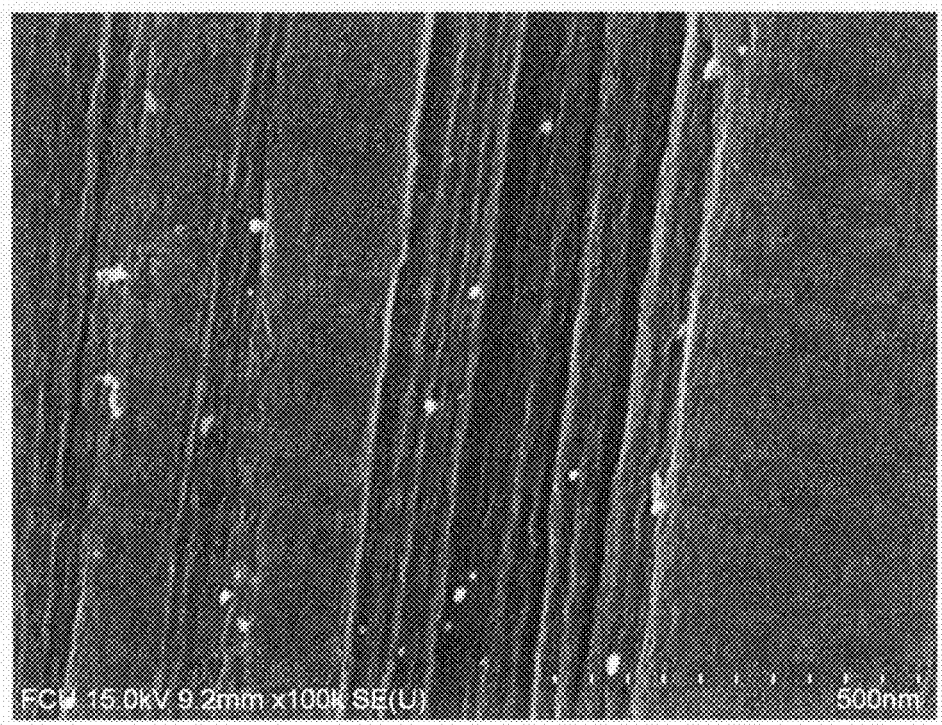
FIG. 1 shows a scanning electronic microscope picture of the surface of the activated carbon fiber obtained in Example 1, wherein the granular white dots are silver particles.

In the method of the subject invention, a carbonaceous material is impregnated in a metal-containing aqueous solution, thereby, the metal is reduced onto the surface of the carbonaceous material. Using silver as an example, Y. L. Wong, Y. Z. Wan, X. H. Dong, G. X. Cheng, H. M. Tao, and T. Y. Wen mentioned such a reduction in *Carbon*, 36, 1567-1571, 1998. They believed that initially, the silver ions form metal crystal nucleuses at active sites (pore sites) of the carbonaceous material. During the reduction process, the silver metal crystal nucleuses start to migrate and aggregate together to form silver particles on the carbonaceous material. The content of this document is incorporated hereinto for reference.

The metal-containing aqueous solution can be provided by adding a proper water soluble metal compound to water. In this aspect, the "water soluble metal compound" comprises sparingly soluble metal compounds. The metals capable of providing ionic metal in water can be used in the subject invention. For example (but not limited to), the metal compounds listed in the following tables can be used in the subject invention to provide the corresponding metal-containing aqueous solutions.

TABLE 1

| Silver-containing compound | |
|---|---|
| Species | Formula |
| silver nitrate | $AgNO_3$ |
| silver acetate | $Ag(CH_3COO)$ |
| silver phosphate | $Ag_3PO_4$ |
| silver carbonate | $Ag_2CO_3$ |

TABLE 2

| Cobalt-containing compound | |
|---|---|
| Species | Formula |
| cobalt(II) nitrate | $Co(NO_3)_2$ |
| cobalt(III) acetate | $Co(CH_3COO)_3$ |
| cobalt(II) acetate | $Co(CH_3COO)_2$ |
| cobalt(III) carbonate | $CoCO_3$ |
| cobalt(II) sulfate | $CoSO_4$ |
| cobalt(II) fluoride | $CoF_2$ |

TABLE 2-continued

Cobalt-containing compound

| Species | Formula |
| --- | --- |
| cobalt(II) chloride | $CoCl_2$ |
| cobalt(II) bromide | $CoBr_2$ |
| cobalt(II) iodide | $CoI_2$ |
| potassium hexacyanocobaltate(III) | $K_3Co(CN)_6$ |

TABLE 3

Nickel-containing compound

| Species | Formula |
| --- | --- |
| nickel nitrate | $Ni(NO_3)_2$ |
| nickel ammonium nitrate | $Ni(NO_3)_2 \cdot 4NH_3 \cdot 2H_2O$ |
| nickel carbonate | $NiCO_3$ |
| nickel formate | $Ni(HCOO)_2$ |
| nickel sulfate | $NiSO_4$ |
| nickel ammonium sulfate | $NiSO_4 \cdot (NH_4)_2SO_4 \cdot 6H_2O$ |
| nickel sulfide | $NiS$ |
| nickel hydroxide | $Ni(OH)_2$ |
| nickel chloride | $NiCl_2$ |
| nickel bromide | $NiBr_2$ |
| nickel iodide | $NiI_2$ |

TABLE 4

Zinc-containing compound

| Species | Formula |
| --- | --- |
| zinc nitrate | $Zn(NO_3)_2$ |
| zinc nitrite | $Zn(NO_2)_2$ |
| zinc oxalate | $ZnC_2O_4$ |
| zinc phosphite | $ZnHPO_3$ |
| zinc hypophosphite | $Zn(H_2PO_2)_2$ |
| zinc formate | $Zn(HCOO)_2$ |
| zinc lactate | $Zn(C_3H_5O_3)_2$ |
| zinc malate | $Zn(OOCCH_2CHOHCOO) \cdot 3H_2O$ |
| zinc salicylate | $Zn[C_6H_4(OH)COO]_2$ |
| zinc tartrate | $ZnC_4H_4O_6$ |
| zinc caprylate | $Zn(C_7H_{15}COO)_2$ |
| zinc propionate | $Zn(C_2H_5COO)_2$ |
| zinc benzoate | $Zn(C_{14}H_{10}O_4)$ |
| zinc sulfate | $ZnSO_4$ & $ZnSO_4 \cdot 7H_2O$ |
| zinc sulfite | $ZnSO_3 \cdot 2H_2O$ |
| zinc ethylsulfate | $Zn(C_2H_5OSO_3)_2 \cdot 2H_2O$ |
| zinc formaldehyde sulfoxylate | $Zn(HOCH_2SO_2)_2$ |
| zinc thiocyanate | $Zn(SCH)_2$ |
| zinc borate | $3ZnO \cdot 2B_2O_3$ |
| zinc perborate | $Zn(BO_3)_2$ |
| zinc selenate | $ZnSeO_4$ |
| zinc selenide | $ZnSe$ |
| zinc fluoride | $ZnF_2$ |
| zinc fluorosilicate | $ZnSiF_6 \cdot 6H_2O$ |
| zinc hexafluorosilicate | $ZnSiF_6$ |
| zinc chlorate | $Zn(ClO_3)_2 \cdot 4H_2O$ |
| zinc chloride | $ZnCl_2$ |
| zinc perchlorate | $Zn(ClO_4)_2$ |
| zinc bromate | $Zn(BrO_3)_2 \cdot 6H_2O$ |
| zinc bromide | $ZnBr_2$ |
| zinc iodate | $Zn(IO_3)_2$ |
| zinc iodide | $ZnI_2$ |
| zinc dichromate | $ZnCr_2O_7$ |

TABLE 5

Gold-containing compound

| Species | Formula |
| --- | --- |
| ammonium disulfitiaurate(I) | $(NH_4)_3[Au(SO_3)_2]$ |
| sodium bis(thiosulfato)aurate(I) hydrate | $Na_3Au(S_2O_3)_2 \cdot nH_2O$ |
| potassium dicyanoaurate(I) | $K[Au(CN)_2]$ |
| gold chloride | $AuCl$ |
| hydrogen tetrachloroaurate(III) | $H[AuCl_4]$ |
| sodium tetrachloroaurate(III) | $Na[AuCl_4] \cdot nH_2O$ |
| chloro(triphenylphosphine) gold(I) | $Au[Cl(PPh_3)]$ |
| gold tribromide | $AuBr_3$ |
| sodium bromoaurate(III) | $Na[AuBr_4]$ |

TABLE 6

Copper-containing compound

| Species | Formula |
| --- | --- |
| copper acetate | $Cu(CH_3COO)_2 \cdot H_2O$ |
| copper acetylacetonate | $Cu(C_5H_7O_2)$ |
| copper(II) hydroxide | $Cu(OH)_2$ |
| copper(II) fluoride | $CuF_2$ |
| copper(I) chloride | $CuCl$ |
| copper(I) bromide | $CuBr$ |

TABLE 7

Platinum-containing compound

| Species | Formula |
| --- | --- |
| platinum(II) nitrate | $Pt(NO_3)_2$ |
| platinum sulfite | $Pt(SO_3)_x$ (x = 1 or 2) |
| platinum(II) chloride | $PtCl_2$ |
| platinum(IV) chloride | $PtCl_4$ |
| ammonium hexachloroplatinate (IV) | $(NH_4)_2PtCl_6$ |
| dihydrogen hexachloroplatinate(IV) | $H_2[PtCl_6]$ <br> $H_2[PtCl_6] \cdot H_2O$ |
| sodium tetrachloroplatinate(II) | $Na_2[PtCl_4]$ <br> $Na_2[PtCl_4] \cdot H_2O$ |
| tetraamineplatinum(II) chloride | $[Pt(NH_3)_4]Cl$ <br> $[Pt(NH_3)_4]Cl \cdot nH_2O$ |
| bis(acetylacetonato) platinum(II) | $Pt(C_5H_7O_2)_2$ |
| cis-diaminedichloro platinum(II) | cis-$[PtCl_2(NH_3)_2]$ |
| cis-diaminedinitrito platinum(II) | cis-$[Pt(NO_2)_2(NH_3)_2]$ |
| cis-dichloro-bis(triphenylphosphate) platinum(II) | cis-$[PtCl_2(PPh_3)_2]$ |
| di-m-chloro-bis[chloro(cyclohexene)-platinum(II)] | $[\{PtCl(C_6H_{10})\}_2(m\text{-}Cl)_2]$ |
| dichloro (cycloocta-1,5-diene)-platinum(II) | $[PtCl_2(C_8H_{12})]$ |
| dihydrogen hexahydroxoplatinate(IV) | $H_2[Pt(OH)_6]$ |
| platinum(0) divinyltetramethyl-disiloxane complex | $[Pt_2(C_8H_{18}OSi_2)_3]$ |
| potassium hexahydroxoplatinate(IV) | $K_2[Pt(OH)_6]$ |
| potassium tetracyanoplatinate(II) hydrate | $K_2[Pt(CN)_4] \cdot nH_2O$ |
| tetraaminplatinum(II) hydrogencarbonate | $[Pt(NH_3)_4](HCO_3)_2$ |
| tetraamineplatinum(II) hydrogenphosphate | $[Pt(NH_3)_4]HPO_4$ |
| tetraamineplatinum(II) hydroxide | $[Pt(NH_3)_4](OH)_2$ |
| tetraamineplatinum(II) nitrate | $[Pt(NH_3)_4](NO_3)_2$ |

TABLE 8

Palladium-containing compound

| Species | Formula |
| --- | --- |
| palladium(II) nitrate | $Pd(NO_3)_2$ <br> $Pd(NO_3)_2 \cdot H_2O$ |
| palladium(II) acetate | $Pd(CH_3COO)_2$ |
| palladium(II) chloride | $PdCl_2$ |

TABLE 8-continued

Palladium-containing compound

| Species | Formula |
| --- | --- |
| palladium(II) bromide | $PdBr_2$ |
| bis(acetonitrile) dichloropalladium(II) | $[PdCl_2(CH_3CN)_2]$ |
| bis(acetylacetonato) palladium(II) | $[Pd(C_5H_7O_2)_2]$ |
| bis(dibenzylideneacetone) palladium(0) | $Pd(C_{17}H_{14}O)_2$ |
| bis(ethylenediamine) palladium(II) chloride | $[Pd(C_2H_8N_2)_2]Cl_2$ |
| diamminedichloro palladium(II) | $[PdCl_2(NH_3)_2]$ |
| diaminedinitritopalladium(II) | $[Pd(NO_2)_2(NH_3)_2]$ |
| dichlorobis (triphenylphosphine) palladium(II) | $[PdCl_2(PPh_3)_2]$ |
| dichloro (cycloocta-1,5-diene) palladium(II) | $PdCl_2(C_8H_{12})$ |
| dichloro[1,1'-ferrocenylbis (diphenylphosphine)] palladium(II) dichloromethane | $[(C_5H_4P(C_6H_5)_2)_2Fe]PdCl_2$ |
| dihydrogen tetrachloropalladate(II) | $H_2[PdCl_4]$ |

TABLE 9

Iron-containing compound

| Species | Formula |
| --- | --- |
| ferric nitrate | $Fe(NO_3)_3 \cdot 9H_2O$ |
| ferric(III) citrate | $FeC_6H_5O_7 \cdot 5H_2O$ |
| ferric ammonium citrate | $(NH_4)_3Fe(C_6H_5O_7)_2$ |
| ferric ammonium oxalate | $(NH_4)_3Fe_2(C_2O_4)_3 \cdot 3H_2O$ |
| sodium ferric oxalate | $Na_3Fe(C_2O_4)_3 \cdot 5.5H_2O$ |
| ferric oxalate | $Fe_2(C_2O_4)_3$ |
| ferrous acetate | $Fe(CH_3COO)_2$ |
| ferric glycerophosphate | $Fe_2[CH_2H_5(OH)_2PO_4]_3 \cdot nH_2O$ |
| ferric hypophosphite | $Fe(H_2PO_2)_3$ |
| ferric dichromate | $Fe_2(Cr_2O_7)_3 \cdot nH_2O$ |
| ferric sulfate | $Fe_2(SO_4)_3$ |
| iron sulfate | $FeSO_4$ |
| ferrous sulfate | $FeSO_4 \cdot 7H_2O$ |
| ferrous ammonium sulfate | $FeSO_4 \cdot (NH_4)_2SO_2 \cdot 6H_2O$ |
| ferric ammonium sulfate | $FeNH_4(SO_4)_2 \cdot 12H_2O$ |
| ferrous gluconate | $Fe(C_6H_{11}O_7)_2 \cdot 2H_2O$ |
| ferrous lactate | $Fe(CH_3CHOHCOO)_2 \cdot 9H_2O$ |
| ferrous fumarate | $FeC_4H_2O_4$ |
| ferrous fluoride | $FeF_3$ |
| iron chloride | $FeCl_2$ |
| | $FeCl_2 \cdot 4H_2O$ |
| iron chloride | $FeCl_3$ |
| | $FeCl_3 \cdot 6H_2O$ |
| ferrous bromide | $FeBr_2 \cdot 6H_2O$ |
| ferrous iodide | $FeI_2 \cdot 4H_2O$ |

According to one embodiment of the subject invention, a carbonaceous material carrying one metal is prepared. The material can be prepared by for example, but is not limited to, the following manners. If a silver-carrying carbonaceous material is required, an aqueous solution of silver nitrate can be used. If a cobalt-carrying carbonaceous material is required, an aqueous solution of cobalt nitrate can be used. If a nickel-carrying carbonaceous material is required, an aqueous solution of nickel nitrate can be used. Moreover, the aqueous solution for impregnation can also comprise two or more metals to provide a carbonaceous material carrying two or more metals. Such material can be prepared by for example, but is not limited to, the following manners. If the metal-containing aqueous solution comprises silver nitrate and cobalt nitrate, a carbonaceous material comprising silver and cobalt can be produced. If the metal-containing aqueous solution comprises silver nitrate and nickel nitrate, a carbonaceous material comprising silver and nickel can be produced. Also, if the metal-containing aqueous solution comprises silver nitrate and zinc chloride, a carbonaceous material comprising silver and zinc can be produced. Other embodiments of the carbonaceous materials comprising two or more metals according to the subject invention can be inferred from above, and are not further described herein.

The amount of the metal-containing aqueous solution is not critical to the subject invention. However, for economic concern, the amount of the metal compound added to an aqueous solution is generally not above that required for providing a saturated concentration. Also, it is possible to add the metal compound in an amount exceeding that required for the saturated concentration to readily supply the dissolved metal amount which is decreased due to the reduction of metal onto the carbonaceous material. Typically, the concentration of the metal compound in the aqueous solution ranges from 0.0001 to 10 mol/L, preferably from 0.001 to 1 mol/L.

It has been found that if the carbonaceous material is directly impregnated in the metal-containing aqueous solution, the carbonaceous material will adsorb bubbles because of capillarity. The bubbles will hinder the metal from being reduced and carried onto the surface of the carbonaceous material. To avoid the adverse effects because of capillarity, the impregnation step (a) should be conducted under at least one of these: (a1) under vacuum, (a2) with stirring, and (a3) with the addition of a polar solvent.

If the vacuum manner is used to avoid capillarity, the impregnation time is normally at least 1 minute, e.g., 1 to 720 minutes, preferably 60 to 720 minutes, and more preferably 180 to 720 minutes. If the stirring manner is used, the rational speed preferably ranges from 0.5 to 5000 rpm for at least 5 minutes, e.g., 5 minutes to 48 hours. In this aspect, if the above two manners are used together, i.e., the impregnation being conducted under vacuum and with stirring, the impregnation time can be shortened.

Another manner for avoiding the capillarity is the addition of an organic polar solvent to the metal-containing aqueous solution. Without being limited by the theory, it is believed that the polar solvent can promote the adsorption between the metal and the surface of the carbonaceous material such that the metal particles are uniformly distributed on the surface of the carbonaceous material and their amount carried on the material is increased. Any proper polar solvents can be used in the subject invention, such as alcohol, aldehyde, ketone, ether, and a combination thereof The polar solvent can be selected from a group consisting of, for example, but is not limited to: $C_1$-$C_4$ alcohol, $C_1$-$C_4$ aldehyde, $C_3$-$C_6$ ketone, $C_1$-$C_4$ ether, and a combination thereof. Preferably, the polar solvent is selected from a group consisting of: ethanol, acetone, and a combination thereof. The amount of the polar solvent in the metal-containing aqueous solution is not critical to the subject invention. In general, the amount of the polar solvent ranges from 5 to 70 vol %, preferably from 8 to 60 vol %, and more preferably from 10 to 55 vol %, based on the total amount of the solvent and water. The impregnation time required is normally at least 5 minutes, e.g., 5 to 600 minutes, preferably 5 to 240 minutes, and more preferably 10 to 120 minutes. The operation of adding a polar solvent is optionally used in combination with the vacuum means and/or stirring manner.

According to one preferred embodiment of the subject invention, the impregnation step (a) is conducted with (a2) stirring and (a3) the addition of a polar solvent. The impregnation time is normally at least 1 minute, e.g., 1 to 360 minutes, preferably 5 to 240 minutes, and more preferably 10 to 120 minutes.

After the impregnation step is finished, the impregnated carbonaceous material is thermally treated at a temperature ranging from 120° C. to a temperature not higher than the melting point of the involved metal. The metal reduced onto the surface of the carbonaceous material is then thermally cracked into fine particles. For example, if the involved metal is silver, the thermal treatment is preferably conducted at a temperature ranging from 200° C. to 900° C., and more preferably from 500° C. to 700° C. It has been found that if the temperature of the heat treatment is above 500° C., silver particles with a size of less than 50 nm can be obtained on the carbonaceous material, especially on the fibrous carbonaceous material.

Moreover, to avoid the ashing of the carbonaceous material during the thermal treatment, the thermal treatment should be conducted under vacuum or under the protection of an inert gas. The thermal treatment can be conducted in a gas atmosphere selected from a group consisting of, for example, but is not limited to: nitrogen gas, helium gas, argon gas, and a combination thereof. The time required for the thermal treatment normally ranges from 5 to 120 minutes. Optionally, the impregnated carbonaceous material is dried for removing water and then thermally treated. Typically, the drying step is conducted at a temperature ranging from 25° C. to 150° C. Moreover, the drying step can also be conducted with passing gas.

Furthermore, after the thermal treatment, the metal-containing carbonaceous material can be optionally washed with water to remove the metal which is not well adsorbed onto the surface of the carbonaceous material. The time of the washing step normally ranges from 1 minute to 600 hours. Afterwards, the washed carbonaceous material is dried to obtain the product of a metal-containing carbonaceous material.

The following examples are provided to further illustrate the subject invention.

EXAMPLES 1 TO 11

In the following examples, the obtained products were tested by the equipments and methods as follows to measure the metal content and observe the surface of the carbonaceous material.

I. Test of the Metal Content

Equipment:
a. Microwave Lab Station: Milestone Ethos Company, Italy, Model: Terminal 320.
b. Inductively Coupled Plasma Optima Optical Emission Spectrometer, ICP-OES: Perkin Elmer Company, the United States, Model: OPTIMA 2000DV.

Method:
1. A dried metal-carrying carbonaceous material in an amount of 50 mg to 80 mg was placed in a microwave nitrification flask, and then, a nitrification liquid composed of 1 ml of hydrochloric acid, 5 ml of sulfuric acid, 1 ml of hydrochloric acid, and 1 ml of nitric acid was added to the flask. The flask was then sealed.
2. At least 4 flasks were placed in the microwave nitrification machine in a symmetrical arrangement to conduct the nitrification.
3. After the microwave nitrification, the flasks were stood for 3 to 4 hours until the temperature was decreased to room temperature and then taken from the machine.
4. The nitrification liquid was filtered with a No. 40 filter paper. The filtrate was added to a PP centrifugal bottle, and then, deionized water was added thereto until a total amount of 50 ml of the solution was attained. Next, the bottle was cooled in a refrigerator.
5. The ICP-OES standard metal liquids of 0 ppm, 0.05 ppm, 0.1 ppm, 0.5 ppm, 1 ppm, 3 ppm, and 5 ppm were prepared and used as the calibration curve.
6. The solution to be tested was determined with ICP-OES. Each sample was measured 3 to 5 times and an average was calculated. After each measurement, diluent nitric acid and deionized water were alternatively used to wash the machine to avoid influencing subsequent test results.

II. Observation of the Surface of the Carbonaceous Material

Equipment:
Cold Field Emission Scanning Electronic Microscope and Energy Dispersive Spectrometer, Hitachi, Japan, Model: S-4800.

Method:
The metal-carrying carbonaceous material with an appropriate size was fixed on a supporter (diameter: 2.5 cm) using a carbon tape, where the supporter was placed on a heating plate at 80° C. for 1 hour. The observation of the surface of the carbonaceous material was conducted using an accelerating voltage of 10 to 15 kV and a magnifying power of 5000 to 400000. Since the test was to observe the surface configuration of the metal-carrying carbonaceous material, it was unnecessary to plate gold.

Example 1

The activated carbon fiber cloth produced by Challenge Carbon Technology Ltd. (No.: FAW1101, BET: 1050 m$^2$/g) was used as the raw material. The activated carbon fiber cloth was impregnated in a silver nitrate aqueous solution with a concentration of 0.02 M with stirring at 50 rpm for 2 hours. Afterwards, the carbonaceous material was dehydrated and then dried at 120° C. to remove water.

Under the protection of nitrogen gas, the impregnated activated carbon fiber cloth was heated from room temperature to 600° C. at a rate of 4° C./min, thermally cracked at 600° C. for 1 minute, and then cooled to room temperature at a rate of 10° C./min.

Next, the carbonaceous material was washed with water for 2 hours and then dried at 120° C. for 2 hours to obtain the final product. According to the above measurement procedures, the product was tested. The test results showed that the product comprised 0.01 wt % of silver based on its total weight and the silver particles on the activated carbon fiber were a nano size of about 10 to 30 nm, as shown in FIG. 1 (wherein the white circular dots were silver particles).

Example 2

Figure 2:
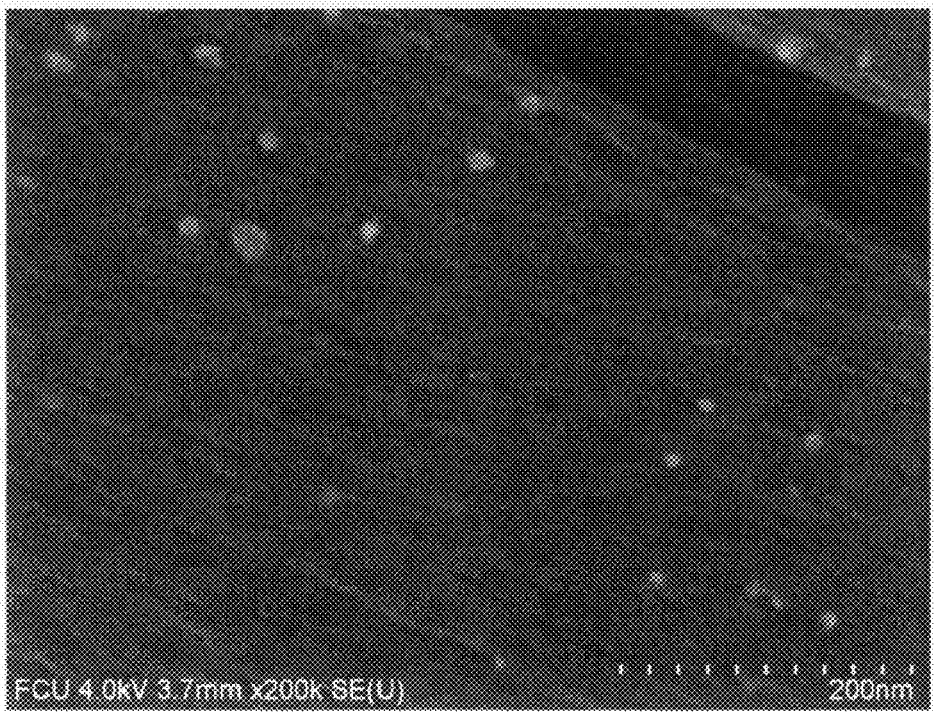
FIG. 2 shows a scanning electronic microscope picture of the surface of the activated carbon fiber obtained in Example 2, wherein the granular white dots are silver particles.

The raw material and preparation conditions were the same as those in Example 1, but the temperature of the thermal cracking was 1000° C. and its time was 1 minute. The test results showed that the product comprised 0.09 wt % of silver based on its total weight and the silver particles on the activated carbon fiber were a nano size of about 20 nm, as shown in FIG. 2 (wherein the white circular dots were silver particles).

Example 3

The raw material was the same as that in Example 1. The activated carbon fiber cloth was impregnated in a silver nitrate aqueous solution with a concentration of 0.02 M and stirred at 50 rpm for 2 hours. The silver nitrate aqueous solution was formulated with ethanol and water in a volume ratio of 1:1, wherein the content of ethanol was 50 vol % based on the total volume of the mixture. The subsequent preparation procedures were the same as those in Example 1.

Figure 3:
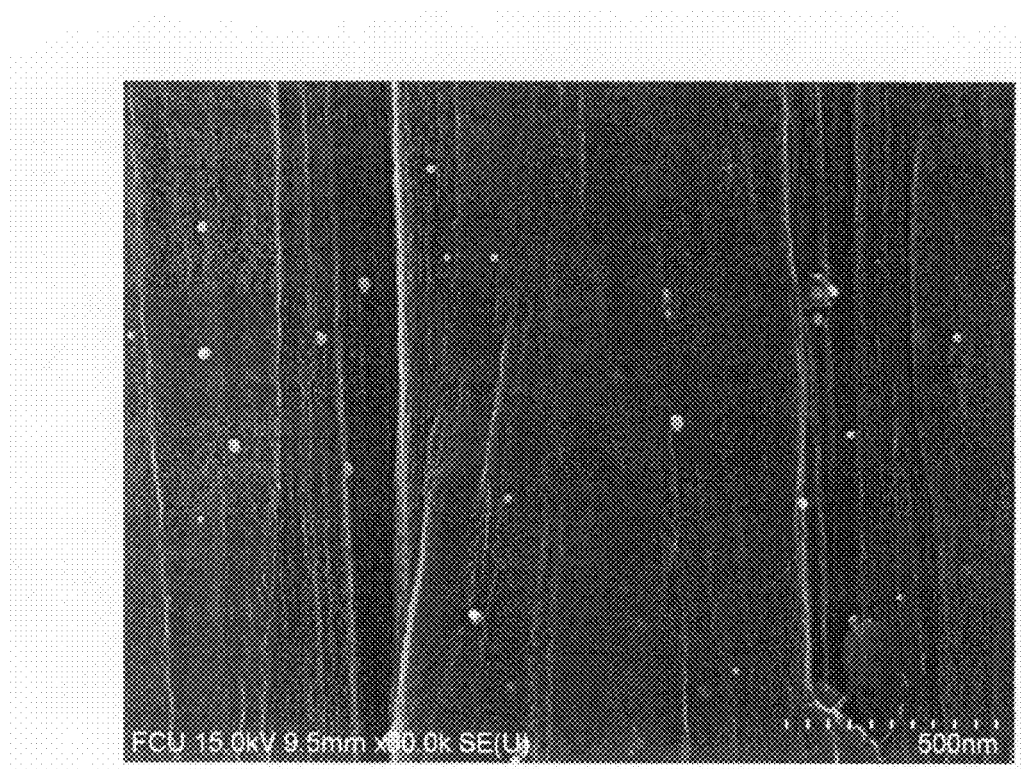
FIG. 3 shows a scanning electronic microscope picture of the surface of the activated carbon fiber obtained in Example 3, wherein the granular white dots are silver particles.

The test results showed that the product comprised 0.20 wt % of silver based on its total weight, and the silver particles on the activated carbon fiber were a nano size of about 10 to 30 nm and more uniformly distributed, as shown in FIG. 3 (wherein the white circular dots were silver particles).

Example 4

Figure 4:
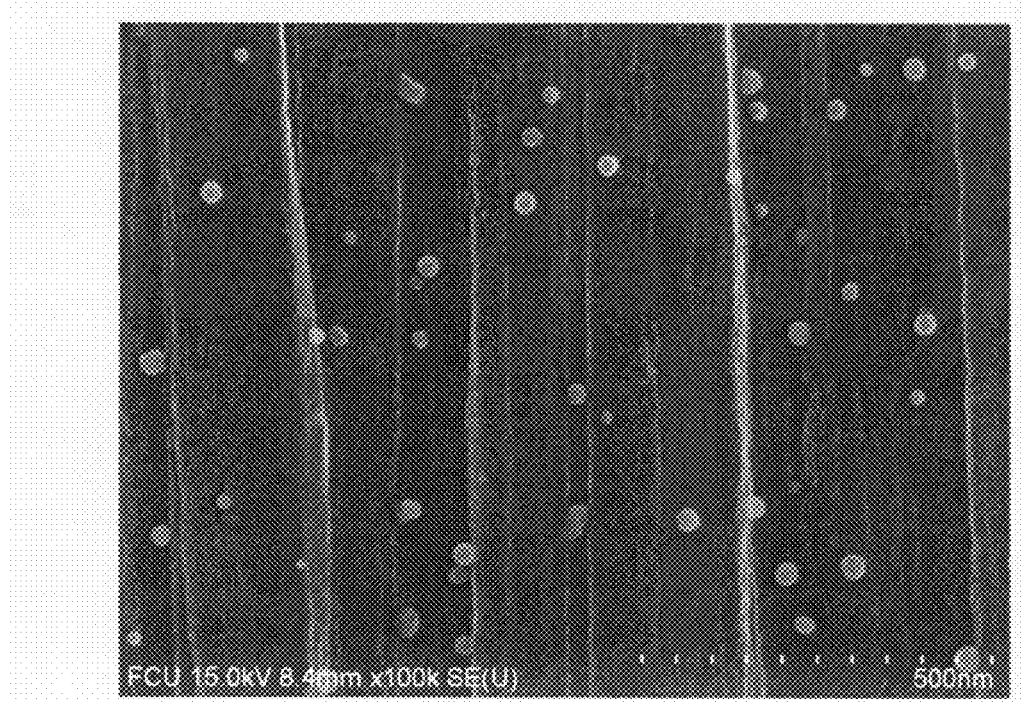
FIG. 4 shows a scanning electronic microscope picture of the surface of the carbon fiber obtained in Example 4, wherein the granular white dots are silver particles.

The procedures illustrated in Example 3 were repeated with the exception that the carbon fiber cloth produced by Challenge Carbon Technology Ltd. (No.: FCW1005) was used as the raw material. The test results showed that the product comprised 0.15 wt % of silver based on its total weight, and the silver particles on the carbon fiber were a nano size of about 20 to 40 nm and more uniformly distributed, as shown in FIG. 4 (wherein the white circular dots were silver particles).

Example 5

Figure 5:
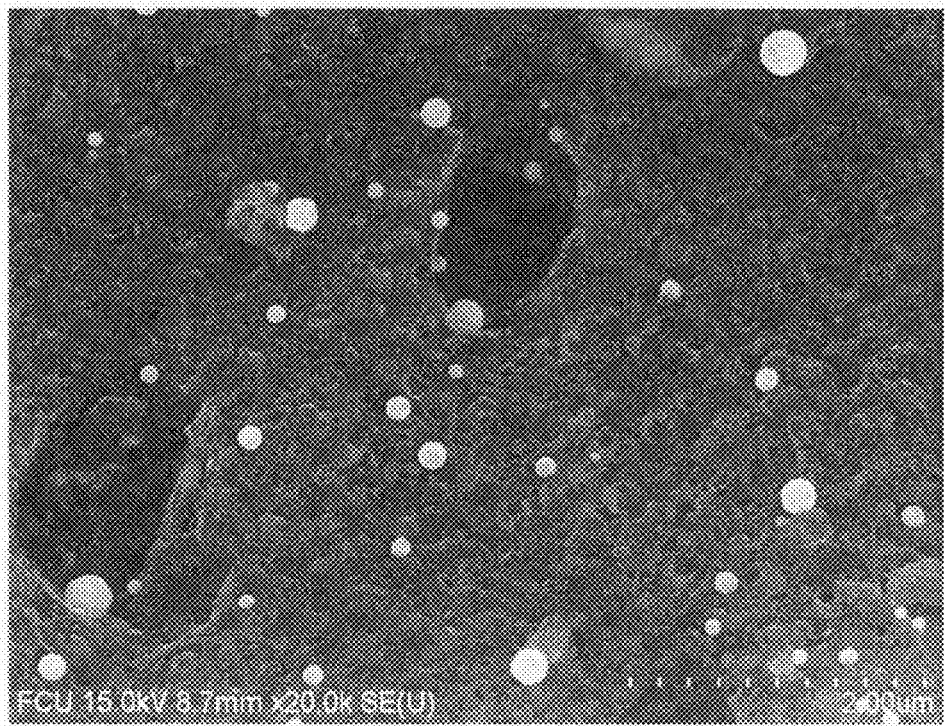
FIG. 5 shows a scanning electronic microscope picture of the surface of the activated carbon fiber obtained in Example 5, wherein the granular white dots are silver particles.

The activated carbon granule produced by Union Chemical Works Ltd. (No.: 79121 Charcoal) was used as the raw material. The production was conducted according to the procedures described in Example 3, but a silver nitrate aqueous solution with a concentration of 0.008 M was used for the impregnation. The test results showed that the product comprised 0.22 wt % of silver based on its total weight, and the silver particles on the activated carbon granule were about 100 to 300 nm, as shown in FIG. 5.

Example 6

The activated carbon fiber cloth produced by Challenge Carbon Technology Ltd. (No.: FAW1101, BET: 1050 $m^2/g$) was used as the raw material. The activated carbon fiber cloth was impregnated in a cobalt nitrate aqueous solution with a concentration of 0.01 M and stirred at 50 rpm for 5 hours. Afterwards, the cloth was dehydrated and then dried at 120° C. to remove water.

Under the protection of nitrogen gas, the impregnated activated carbon fiber cloth was heated from room temperature to 600° C. at a rate of 4° C./min, thermally cracked at 600° C. for 1 minute, and then cooled to room temperature at a rate of 10° C./min.

Next, the cloth was washed with water for 2 hours and then dried at 120° C. for 2 hours to obtain a final product. According to the above measurement procedures, the product was tested. The test results showed that the product comprised 0.18 wt % of cobalt based on its total weight, and the cobalt particles on the activated carbon fiber were about 10 to 50 nm.

Example 7

The activated carbon fiber cloth produced by Challenge Carbon Technology Ltd. (No.: FAW1101, BET: 1050 $m^2/g$) was used as the raw material. The activated carbon fiber cloth was impregnated in a nickel nitrate aqueous solution with a concentration of 0.02 M and stirred at 50 rpm for 1 hour. Afterwards, the cloth was dehydrated and then dried at 120° C. to remove water.

Under the protection of nitrogen gas, the impregnated activated carbon fiber cloth was heated from room temperature to 600° C., thermally cracked at 600° C. for 1 minute, and then cooled to room temperature at a rate of 10° C./min.

Next, the cloth was washed for 2 hours and then dried at 120° C. for 2 hours to obtain a final product. According to the above measurement procedures, the product was tested. The test results showed that the product comprised 0.01 wt % of nickel based on its total weight, and the nickel particles on the activated carbon fiber were about 50 to 100 nm.

Example 8

The activated carbon fiber cloth produced by Challenge Carbon Technology Ltd. (No.: FAW1101, BET: 1050 $m^2/g$) was used as the raw material. The activated carbon fiber cloth was impregnated in a zinc nitrate aqueous solution with a concentration of 0.02 M and stirred at 50 rpm for 5 hours. Afterwards, the cloth was dehydrated and then dried at 120° C. to remove water.

Under the protection of nitrogen gas, the impregnated activated carbon fiber cloth was heated from room temperature to 500° C. at a rate of 4° C./min, thermally cracked at 500° C. for 1 minute, and then cooled to room temperature at a rate of 10° C./min.

Figure 6:
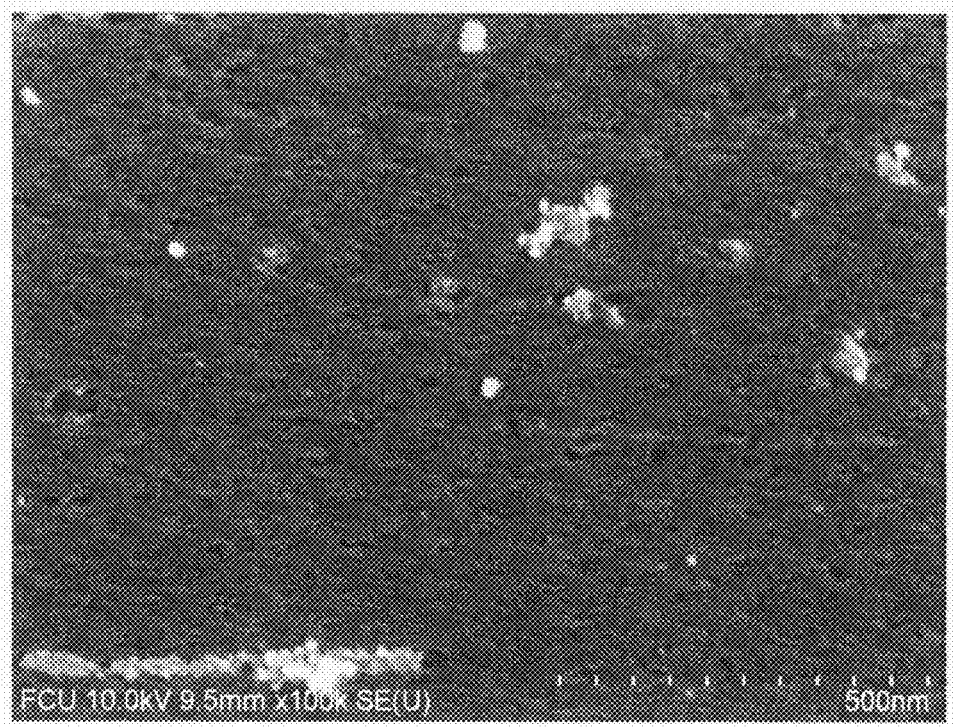
FIG. 6 shows a scanning electronic microscope picture of the surface of the activated carbon fiber obtained in Example 8, wherein the granulated white dots are silver granules.

Next, the cloth was washed with water for 2 hours and then dried at 120° C. for 2 hours to obtain a final product. According to the above measurement procedures, the product was tested. The test results showed that the product comprised 0.64 wt % of zinc based on its total weight and the zinc particles on the activated carbon fiber were about 20 to 50 nm, as shown in FIG. 6.

Example 9

The activated carbon fiber cloth produced by Challenge Carbon Technology Ltd. (No.: FAW1101, BET: 1050 $m^2/g$) was used as the raw material. The activated carbon fiber cloth was impregnated in an aqueous solution of silver nitrate and cobalt nitrate with a concentration of 0.02 M and stirred at 50 rpm for 1 hour. Afterwards, the cloth was dehydrated and then dried at 120° C. to remove water.

Under the protection of nitrogen gas, the impregnated activated carbon fiber cloth was heated from room temperature to 600° C. at a rate of 4° C./min, thermally cracked at 600° C. for 1 minute, and then cooled to room temperature at a rate of 10° C./min.

Next, the cloth was washed with water for 2 hours and then dried at 120° C. for 2 hours to obtain a final product. According to the above measurement procedures, the product was tested. The test results showed that the product comprised 0.06 wt % of silver and 0.11 wt % of cobalt based on its total weight, respectively. The silver and cobalt particles on the activated carbon fiber were about 10 to 50 nm and 50 to 100 nm, respectively.

Example 10

The activated carbon fiber cloth produced by Challenge Carbon Technology Ltd. (No.: FAW1101, BET: 1050 $m^2/g$) was used as the raw material. The activated carbon fiber cloth was impregnated in an aqueous solution of silver nitrate and zinc chloride with a concentration of 0.02 M and stirred at 50 rpm for 1 hour. Afterwards, the cloth was dehydrated and then dried at 120° C. to remove water.

Under the protection of nitrogen gas, the impregnated activated carbon fiber cloth was heated from room temperature to 600° C. at a rate of 4° C./min, thermally cracked at 600° C. for 1 minute, and then cooled to room temperature at a rate of 10° C./min.

Figure 7:
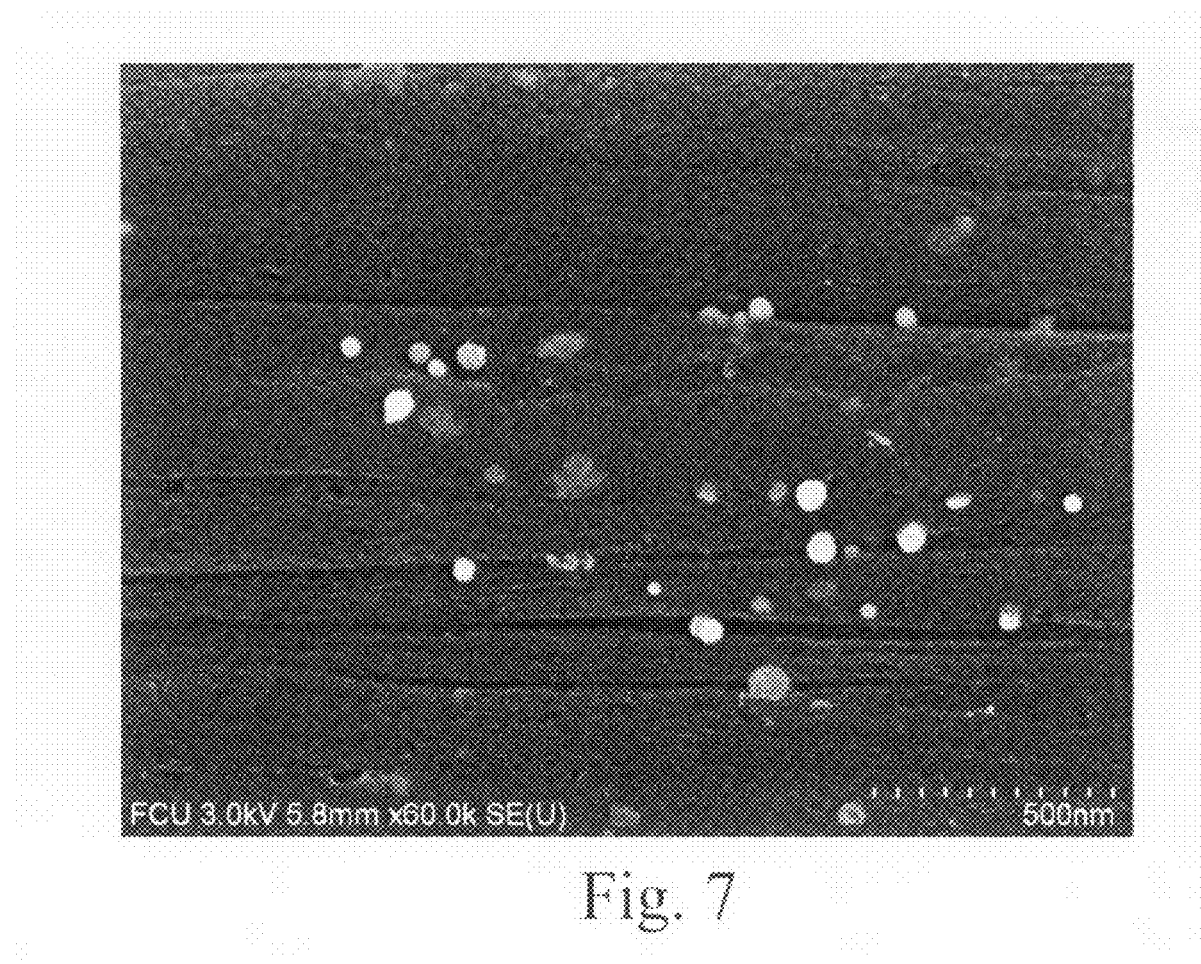
FIG. 7 shows a scanning electronic microscope picture of the surface of the activated carbon fiber obtained in Example 10, wherein the brighter dots are silver and the darker and bigger ones are zinc.

Next, the cloth was washed with water for 2 hours and then dried at 120° C. for 2 hours to obtain a final product. According to the above measurement procedures, the product was tested. The test results showed that the product comprised 0.011 wt % of silver and 0.81 wt % of zinc based on its total weight, respectively. The silver and zinc particles on the activated carbon fiber were about 10 to 50 nm and 50 to 100 nm, respectively. As shown in FIG. 7, the brighter dots were silver and the darker and bigger dots were zinc.

Example 11

The activated carbon fiber cloth produced by Challenge Carbon Technology Ltd. (No.: FAW1101, BET: 1050 $m^2/g$) was used as the raw material. The activated carbon fiber cloth was impregnated in an aqueous solution of silver nitrate and nickel nitrate with a concentration of 0.02 M and stirred at 50 rpm for 1 hour. Afterwards, the cloth was dehydrated and then dried at 120° C. to remove water.

Under the protection of nitrogen gas, the impregnated activated carbon fiber cloth was heated from room temperature to 600° C. at a rate of 4° C./min, thermally cracked at 600° C. for 1 minute, and then cooled to room temperature at a rate of 10° C./min.

Next, the cloth was washed with water for 2 hours and then dried at 120° C. for 2 hours to obtain a final product. The product was tested according to the above measurement procedures. The test results showed that the product comprised 0.04 wt % of silver and 1.46 wt % of nickel based on its total weight, respectively, and the silver and nickel particles on the activated carbon fiber were about 10 to 50 nm and 10 to 50 nm, respectively.

EXAMPLE 12 TO 19

In the following examples, the obtained products were tested by the equipments and methods as follows to measure the metal content and observe the surface of the carbonaceous material.

I. Test of Metal Content
Equipment:
Atomic Absorption Sectrophometry: Hitachi Company, Japan, Polarized Zeeman Atomic Absorption Sectrophometry, Z8000 System.
Method:
1. Nitrification extraction of silver: a silver-carrying carbonaceous material in an amount of about 4 g to 5 g was ashed in the air under 800° C. for 6 hours. The obtained ash was dissolved in 50 ml of 10 vol % $HNO_3$ solution.
2. A standard solution of silver ions was formulated for providing a calibration curve.
3. The silver content was measured by a flame-type atomic absorption sectrophometry. The combustion-supporting gas was air and the flue was acetylene gas.

II. Observation of the Surface of the Carbonaceous Material
Equipment:
Scanning Electronic Microscope (SEM), Hitachi, Japan, Model: S520.
Method:
The sample was dried at 120° C. for 12 hours and then plated with gold using a sputter coater to form a film with a thickness of about 20 nm. By observing the surface configuration, the size and distribution of the silver particles can be found.

Example 12

The polyacrylonitrile based activated carbon fiber cloth produced by Taiwan Carbon Technology Co. Ltd. (Model: AW1501) was used the raw material. The cloth was impregnated in a silver nitrate aqueous solution with a concentration of 0.1 M and a pH of 3.8 for 5 hours. Afterwards, the cloth was dehydrated and then dried at 120° C. for 2 hours to remove water. Next, the impregnated activated carbon fiber cloth was placed in a stove filled with nitrogen gas under 400° C. for 90 minutes for thermal cracking.

The silver content of the product was tested. The results showed that the product comprised 12.5 wt % of silver based on its total weight and the silver particles were about 50 to 200 nm.

Example 13

The raw material and the preparation conditions were the same as those in Example 12, but after the high temperature thermal cracking, the silver-carrying activated carbon fiber cloth was washed with water in a flow rate of 4.5 L/min for 120 hours and then dried at 120° C. for 2 hours to obtain a final product. The results of testing the silver content showed that the product comprised 0.03 wt % of silver based on its total weight, and the silver particles were about 50 to 200 nm.

Example 14

The raw material and the preparation conditions were the same as those in Example 13, but the cloth was washed with water for 10 days. The test results showed that the product comprised 0.03 wt % of silver based on its total weight, and the silver particles were about 50 to 200 nm.

Example 15

The raw material was the same as that in Example 13. The activated carbon fiber cloth was impregnated in a silver nitrate aqueous solution with a concentration of 0.001 M and a pH of 6.4 for 5 hours. Afterwards, the cloth was dehydrated and then dried at 120° C. for 2 hours to remove water. Next, the impregnated activated carbon fiber cloth was placed in a stove filled with nitrogen gas under 400° C. for 90 minutes for thermal cracking.

Lastly, the silver content was tested. The test results showed that the product comprised 0.53 wt % of silver based on its total weight, and the silver particles were about 50 to 200 nm.

Example 16

The raw material and the preparation procedures were the same as those in Example 15, but after the high temperature thermal cracking, the silver-carrying activated carbon fiber cloth was washed with water in a flow rate of 4.5 L/min for 1 day and then dried at 120° C. for 2 hours to provide a final product. The test results showed that the product comprised 0.23 wt % of silver based on its total weight, and the silver particles were about 50 to 200 nm.

Example 17

The raw material and the preparation procedures were the same as those in Example 16, but the cloth was washed with water for 10 days. The test results showed that the product comprised 0.075 wt % of silver based on its total weight, and the silver particles were about 50 to 200 nm.

Example 18

The polyacrylonitrile-based activated carbon fiber felt (BET: 600 $m^2/g$), which was prepared by activating a fireresistant fiber felt at 800° C. for 10 minutes using steam, was used as the raw material. The felt was impregnated in a silver nitrate solution with a concentration of 0.001 M and a pH of 6.4 for 5 hours. Afterwards, the felt was dehydrated and then dried at 120° C. for 2 hours to remove water. Next, the impregnated activated carbon fiber felt was placed in a stove filled with nitrogen gas under 400° C. for 90 minutes for thermal cracking. Afterwards, the activated carbon fiber felt was washed with water in a flow rate of 4.5 L/min for 3 days and then dried at 120° C. for 2 hours to obtain a final product. The test results showed that the product comprised 0.075 wt % of silver based on its total weight, and the silver particles were about 50 to 200 nm.

Example 19

The procedures illustrated in Example 18 were repeated with the exception that the phenolic activated carbon fiber felt produced by Gun Ei Chemical Industry Co., Ltd. (Japan) (Model: CAN-210-15) was used as the material. The results showed that the product comprised 0.072 wt % of silver based on its total weight, and the silver particles were about 50 to 200 nm.

Based on the above examples, it can be found that the subject invention impregnates a carbonaceous material in a metal-containing solution under vacuum, with stirring, and/or with the addition of a polar solvent to reduce the metal onto the surface of the carbonaceous material. The metal is thermally cracked and reduced onto the carbonaceous material to form fine particles using heat treatment at a temperature ranging from 120° C. to a temperature not higher than the melting point of the involved metal. Therefore, a carbonaceous material adsorbing fine metal particles thereon is provided.

The above examples are provided to illustrate the embodiments of the subject invention and show its technical features, but not to limit the scope of protection of the subject invention. Any changes or equivalent arrangements easily accomplished by persons having ordinary skill in the art are within the scope of the subject invention. Consequently, the scope of protection of the present invention is based on the claims attached.

What is claimed is:

1. A method for manufacturing a metal-carrying carbonaceous material comprising:
   (a) impregnating a carbonaceous material in an aqueous solution containing a metal-containing compound;
   (b) thermally treating the impregnated carbonaceous material at a temperature at least 600° C. but not higher than the melting point of the metal under vacuum or in the presence of an inert gas, wherein step (a) is conducted under one or more of the following conditions:
   (a1) under vacuum;
   (a2) with stirring; and
   (a3) with the presence of a polar solvent in the aqueous solution;
   wherein the metal is selected from the group consisting of: silver, cobalt, nickel, zinc, gold, copper, platinum, palladium, iron, and a combination thereof; and
   wherein the metal-containing compound is a nitrate compound.

2. The method of claim 1, wherein the carbonaceous material is selected from the group consisting of: activated carbon, graphite, carbon, and a combination thereof.

3. The method of claim 1, wherein the carbonaceous material is in a form of powder, granule, fiber, or sheet.

4. The method of claim 1, wherein the carbonaceous material is a product of activated carbon or porous graphite.

5. The method of claim 1, wherein the metal is selected from the group consisting of: silver, cobalt, nickel, zinc, and a combination thereof.

6. The method of claim 1, wherein the metal-containing aqueous solution used in step (a) is provided by adding a water soluble compound containing said metal to water.

7. The method of claim 6, wherein the water soluble compound is selected from the group consisting of: silver nitrate, cobalt nitrate, nickel nitrate, zinc nitrate, and a combination thereof.

8. The method of claim 7, wherein the water soluble compound is selected from the group consisting of: silver nitrate, cobalt nitrate, nickel nitrate, zinc nitrate, and a combination thereof.

9. The method of claim 1, wherein step (a) is conducted under condition (a2) and the stirring time ranges from 5 minutes to 48 hours.

10. The method of claim 1, wherein step (a) is conducted under condition (a3) and the polar solvent is selected from the group consisting of: alcohol, aldehyde, ketone, ether, and a combination thereof.

11. The method of claim 10, wherein the polar solvent is selected from the group consisting of: C~-C4 alcohol, C~-C4 aldehyde, C3-C6 ketone, C~-C4 ether, and a combination thereof.

12. The method of claim 11, wherein the polar solvent is selected from the group consisting of: ethanol, acetone, and a combination thereof.

13. The method of claim 10, wherein the polar solvent is in a concentration of 5 to 70 vol % based on the total volume of the polar solvent and water.

14. The method of claim 13, wherein the polar solvent is in a concentration of 10 to 55 vol % based on the total volume of the polar solvent and water.

15. The method of claim 1, wherein the aqueous solution comprises silver and step (b) is conducted at a temperature ranging from 600° C. to 900° C.

16. The method of claim 15, wherein step (b) is conducted at a temperature ranging from 600° C. to 700° C.

17. The method of claim 1, wherein step (b) is conducted under vacuum.

18. The method of claim 1, wherein step (b) is conducted in an inert gas selected from the group consisting of: nitrogen gas, helium gas, argon gas, and a combination thereof.

19. The method of claim 1, wherein after step (b), the method further comprises a step of washing the carbonaceous material.

20. The method of claim 1, wherein after step (a) and before step (b), the method further comprises a step of drying the carbonaceous material.

21. The method of claim 20, wherein the drying step is conducted at a temperature ranging from 25° C. to 150° C.

22. The method of claim 1, wherein step (a) is conducted under condition (a2) and condition (a3).

23. The method of claim 22, wherein the impregnation time ranges from 1 minute to 360 minutes.

* * * * *